(12) United States Patent
Fetvedt

(10) Patent No.: US 8,511,148 B2
(45) Date of Patent: Aug. 20, 2013

(54) DISSOLUTION TEST VESSEL WITH INTEGRAL CENTERING

(75) Inventor: Jeremy Fetvedt, Raleigh, NC (US)

(73) Assignee: Agilent Technologies, Inc., Santa Clara, CA (US)

(*) Notice: Subject to any disclaimer, the term of this patent is extended or adjusted under 35 U.S.C. 154(b) by 508 days.

(21) Appl. No.: 12/625,391

(22) Filed: Nov. 24, 2009

(65) Prior Publication Data

US 2011/0120239 A1 May 26, 2011

(51) Int. Cl.
  *G01N 1/00* (2006.01)
(52) U.S. Cl.
  USPC ........................... 73/64.56; 73/864.91
(58) Field of Classification Search
  USPC ................... 73/864.91, 866, 64.56
  See application file for complete search history.

(56) References Cited

U.S. PATENT DOCUMENTS

| | | | |
|---|---|---|---|
| 5,383,745 A * | 1/1995 | Shannon ..................... | 405/52 |
| 5,403,090 A | 4/1995 | Hofer et al. | |
| 5,589,649 A | 12/1996 | Brinker et al. | |
| 6,303,909 B1 | 10/2001 | Fernando et al. | |
| 6,562,301 B1 | 5/2003 | Dean et al. | |
| 6,673,319 B2 | 1/2004 | Dean et al. | |
| 6,727,480 B2 | 4/2004 | Fernando et al. | |
| 6,962,674 B2 | 11/2005 | Dean et al. | |
| 2007/0062841 A1 * | 3/2007 | Nakamura et al. ............ | 206/562 |
| 2009/0207691 A1 | 8/2009 | Fetvedt | |
| 2009/0208377 A1 | 8/2009 | Fetvedt | |
| 2009/0209373 A1 | 8/2009 | Brodmann et al. | |

OTHER PUBLICATIONS

"Varian Dissolution Source Book", 2007-2008, pp. 21-29.

* cited by examiner

*Primary Examiner* — Hezron E Williams
*Assistant Examiner* — Paul West

(57) ABSTRACT

A vessel includes a cylindrical section, a bottom section, a lower ring, and an upper ring. The cylindrical section includes an inside and, an outside vessel surfaces, an upper end region terminating at a rim circumscribing a vessel opening, a vessel groove formed at the outside vessel surface in the upper end region, and a lower end region axially spaced from the upper end region. The bottom section is disposed at the lower end region. The lower ring includes annular lateral and an annular flange portions. The lateral portion is disposed in the vessel groove and includes an outer lateral surface concentric with the inside vessel surface. The flange portion includes an upper and a lower flange surfaces perpendicular to the inside vessel surface. The upper ring includes an inner section extending over at least a portion of the rim, and an outer section securely engaging the upper flange surface.

13 Claims, 6 Drawing Sheets

DISSOLUTION TEST VESSEL WITH INTEGRAL CENTERING

FIELD OF THE INVENTION

The present invention relates generally to dissolution testing of analyte-containing media. More particularly, the present invention relates to the centering and alignment of a vessel utilized to contain dissolution media with respect to an aperture in which the vessel is mounted or an instrument inserted in the vessel.

BACKGROUND OF THE INVENTION

Dissolution testing is often performed as part of preparing and evaluating soluble materials, particularly pharmaceutical dosage forms (e.g., tablets, capsules, and the like) consisting of a therapeutically effective amount of active drug carried by an excipient material. Typically, dosage forms are dropped into test vessels that contain dissolution media of a predetermined volume and chemical composition. For instance, the composition may have a pH factor that emulates a gastrointestinal environment. Dissolution testing can be useful, for example, in studying the drug release characteristics of the dosage form or in evaluating the quality control of the process used in forming the dose. To ensure validation of the data generated from dissolution-related procedures, dissolution testing is often carried out according to guidelines approved or specified by certain entities such as United States Pharmacopoeia (USP), in which case the testing must be conducted within various parametric ranges. The parameters may include dissolution media temperature, the amount of allowable evaporation-related loss, and the use, position and speed of agitation devices, dosage-retention devices, and other instruments operating in the test vessel.

As a dosage form is dissolving in the test vessel of a dissolution system, optics-based measurements of samples of the solution may be taken at predetermined time intervals through the operation of analytical equipment such as a spectrophotometer. The analytical equipment may determine analyte (e.g. active drug) concentration and/or other properties. The dissolution profile for the dosage form under evaluation—i.e., the percentage of analytes dissolved in the test media at a certain point in time or over a certain period of time—can be calculated from the measurement of analyte concentration in the sample taken. In one specific method employing a spectrophotometer, sometimes referred to as the sipper method, dissolution media samples are pumped from the test vessel(s) to a sample cell contained within the spectrophotometer, scanned while residing in the sample cell, and in some procedures then returned to the test vessel(s). In another more recently developed method, sometimes referred to as the in situ method, a fiber-optic "dip probe" is inserted directly in a test vessel. The dip probe includes one or more optical fibers that communicate with the spectrophotometer. In the in situ technique, the spectrophotometer thus does not require a sample cell as the dip probe serves a similar function. Measurements are taken directly in the test vessel and thus optical signals rather than liquid samples are transported between the test vessel and the spectrophotometer via optical fibers.

The apparatus utilized for carrying out dissolution testing typically includes a vessel plate having an array of apertures into which test vessels are mounted. When the procedure calls for heating the media contained in the vessels, a water bath is often provided underneath the vessel plate such that each vessel is at least partially immersed in the water bath to enable heat transfer from the heated bath to the vessel media. Alternatively, heating elements may be attached directly to the vessel. In one exemplary type of test configuration (e.g., USP-NF Apparatus 1), a cylindrical basket is attached to a metallic drive shaft and a pharmaceutical sample is loaded into the basket. One shaft and basket combination is manually or automatically lowered into each test vessel mounted on the vessel plate, and the shaft and basket are caused to rotate. In another type of test configuration (e.g., USP-NF Apparatus 2), a blade-type paddle is attached to each shaft, and the pharmaceutical sample is dropped into each vessel such that it falls to the bottom of the vessel. When proceeding in accordance with the general requirements of Section <711> (Dissolution) of USP24-NF19, each shaft must be positioned in its respective vessel so that its axis is not more than 2 mm at any point from the vertical axis of the vessel.

It is therefore a criterion in certain uses of vessels in which instruments operate that the vessel, and especially its inner surfaces, be aligned concentrically with respect to the instrument. Various approaches have been taken to assist in meeting this criterion, including those disclosed in U.S. Pat. No. 5,403,090, U.S. Pat. No. 6,562,301, U.S. Pat. No. 6,673,319, and U.S. Patent App. Pub. No. 2009/0208377, all assigned to the assignee of the present disclosure. Another approach to vessel alignment is disclosed in U.S. Pat. No. 5,589,649. Yet another approach to vessel alignment is the EaseAlign™ vessel centering ring commercially available from Varian, Inc., Palo Alto, Calif. In addition to concentricity, the verticality of the vessel has an effect on its proper alignment relative to instruments. In the present context, "verticality" generally refers to the precision with which the inside surface of the vessel is truly vertical, or the degree to which the inside surface is truly parallel with the central axis of the vessel or with an elongated instrument inserted into the vessel along the central axis. Regardless of the means taken to ensure that the vessel is concentrically positioned within the aperture of a vessel plate in which the vessel is mounted, if the vessel is not accurately vertical than it is still not aligned accurately. As a result, the inside surface of the vessel will not be precisely parallel with a shaft-based instrument that is intended to be inserted along the central axis of the vessel, and the radial distance between the shaft and the inside surface of the vessel will vary at different elevational points along the central axis and/or at different circumferential positions relative to the central axis.

Accordingly, there is a need for a vessel capable of providing accurate concentricity and verticality when mounted in a vessel supporting structure such as may be included in a dissolution testing apparatus.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a vessel includes a cylindrical section coaxially disposed about a central axis of the vessel, a bottom section, a lower ring, and an upper ring. The cylindrical section includes an inside vessel surface, an outside vessel surface, an upper end region terminating at a rim that circumscribes a vessel opening, a vessel groove formed at the outside vessel surface in the upper end region, and a lower end region axially spaced from the upper end region. The bottom section is disposed at the lower end region. The lower ring includes annular lateral portion and an annular flange portion. The lateral portion is disposed in the vessel groove and includes an outer lateral surface concentric with the inside vessel surface. The flange portion includes an upper flange surface and a lower flange surface perpendicular to the inside vessel surface. The upper ring includes an inner section extending over at least a portion of the rim, and an outer section securely engaged with the upper flange surface.

According to another implementation, a dissolution test apparatus includes a vessel support member and a vessel. The vessel support member includes a top surface and an inside edge circumscribing an aperture. The vessel extends through the aperture. The vessel includes a cylindrical section coaxially disposed about a central axis of the vessel, a bottom section, a lower ring, and an upper ring. The cylindrical section includes an inside vessel surface, an outside vessel surface, an upper end region terminating at a rim that circumscribes a vessel opening, a vessel groove formed at the outside surface in the upper end region, and a lower end region axially spaced from the upper end region. The bottom section is disposed at the lower end region. The lower ring includes an annular lateral portion and an annular flange portion. The lateral portion is disposed in the vessel groove. The lateral portion includes an outer lateral surface concentric with the inside vessel surface. The outer lateral surface contacts the inside edge of the aperture. The flange portion includes an upper flange surface and a lower flange surface perpendicular to the inside vessel surface. The upper ring includes an inner section extending over at least a portion of the rim, and an outer section securely engaged with the upper flange surface. The inside vessel surface is parallel to the inside edge of the vessel support member.

According to another implementation, a method is provided for assembling a vessel. The vessel includes a cylindrical section coaxially disposed about a central axis of the vessel and including an upper end region terminating at a rim circumscribing a vessel opening and a lower end region, and a bottom section disposed at the lower end region. A lower ring is mounted to the vessel such that an annular lateral portion of the lower ring is disposed in a vessel groove formed at an outside vessel surface of the vessel, and an outer lateral surface of the lateral portion is concentric with an inside vessel surface of the vessel. The lower ring further includes a flange portion including a lower flange surface perpendicular to the inside vessel surface. An upper ring is mounted to the vessel such that an inner section of the upper ring extends over at least a portion of the rim, and an outer section of the upper ring is securely engaged with an upper flange surface of the flange portion.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Figure 1:
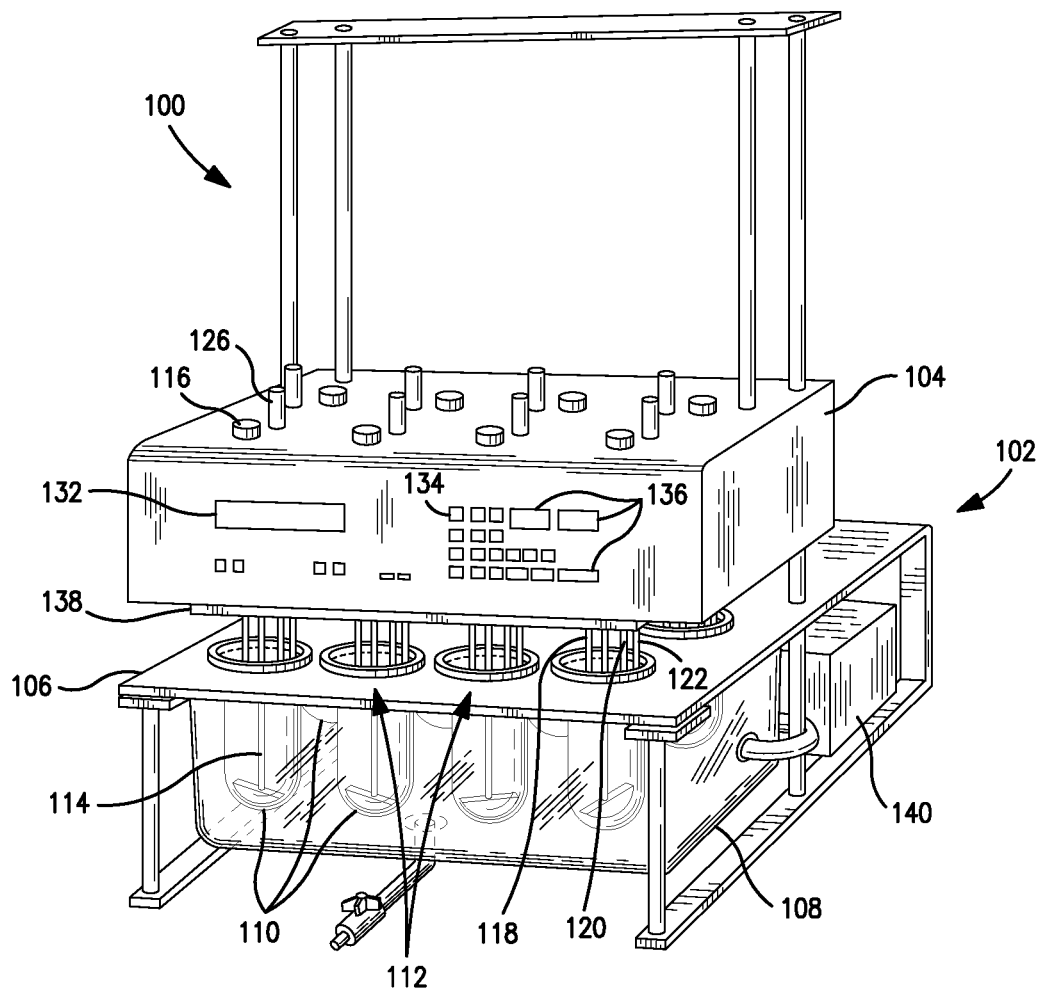
FIG. 1 is a perspective view of an example of a dissolution test apparatus with which vessels taught in the present disclosure may be utilized.

FIG. 1 is a perspective view of an example of a dissolution test apparatus 100 according to an implementation of the present disclosure. The dissolution test apparatus 100 may include a frame assembly 102 supporting various components such as a main housing, control unit or head assembly 104, a vessel support member (e.g., a plate, rack, etc.) 106 below the head assembly 104, and a water bath container 108 below the vessel support member 106. The vessel support member 106 supports a plurality of vessels 110 extending into the interior of the water bath container 108. FIG. 1 illustrates eight vessels 110 by example, but it will be understood that more or less vessels 110 may be provided. The vessels 110 may be centered in place on the vessel support member 106 at a plurality of vessel mounting sites 112 in a manner described in detail below. Vessel covers (not shown) may be provided to prevent loss of media from the vessels 110 due to evaporation, volatility, etc. Optionally, the vessel covers may be coupled to the head assembly 104 and movable by motorized means into position over the upper openings of the vessels 110, as disclosed for example in U.S. Pat. No. 6,962,674, assigned to the assignee of the present disclosure. Water or other suitable heat-carrying liquid medium may be heated and circulated through the water bath container 108 by means such as an external heater and pump module 140, which may be included as part of the dissolution test apparatus 100. Alternatively, the dissolution test apparatus 100 may be a waterless heating design in which each vessel 110 is directly heated by some form of heating element disposed in thermal contact with the wall of the vessel 110, as disclosed for example in U.S. Pat. Nos. 6,303,909 and 6,727,480, assigned to the assignee of the present disclosure.

The head assembly 104 may include mechanisms for operating or controlling various components that operate in the vessels 110 (in situ operative components). For example, the head assembly 104 typically supports stifling elements 114 that include respective motor-driven spindles and paddles operating in each vessel 110. Individual clutches 116 may be provided to alternately engage and disengage power to each stifling element 114 by manual, programmed or automated means. The head assembly 104 also includes mechanisms for driving the rotation of the stifling elements 114. The head assembly 104 may also include mechanisms for operating or controlling media transport cannulas that provide liquid flow paths between liquid lines and corresponding vessels 110. In the present context, the term "between" encompasses a liquid flow path directed from a liquid line into a vessel 110 or a liquid flow path directed from a vessel 110 into a liquid line. Accordingly, the media transport cannulas may include media dispensing cannulas 118 for dispensing media into the vessels 110 and media aspirating cannulas 120 for removing media from the vessels 110. The head assembly 104 may also include mechanisms for operating or controlling other types of in situ operative components 122 such as fiber-optic probes for measuring analyte concentration, temperature sensors, pH detectors, dosage form holders (e.g., USP-type apparatus such as baskets, nets, cylinders, etc.), video cameras, etc. A dosage delivery module 126 may be utilized to preload and drop dosage units (e.g., tablets, capsules, or the like) into selected vessels 110 at prescribed times and media temperatures. Additional examples of mechanisms for operating or controlling various in situ operative components are disclosed for example in above-referenced U.S. Pat. No. 6,962,674.

The head assembly 104 may include a programmable systems control module for controlling the operations of various components of the dissolution test apparatus 100 such as those described above. Peripheral elements may be located on the head assembly 104 such as an LCD display 132 for providing menus, status and other information; a keypad 134 for providing user-inputted operation and control of spindle speed, temperature, test start time, test duration and the like; and readouts 136 for displaying information such as RPM, temperature, elapsed run time, vessel weight and/or volume, or the like.

The dissolution test apparatus 100 may further include one or more movable components for lowering operative components 114, 118, 120, 122 into the vessels 110 and raising operative components 114, 118, 120, 122 out from the vessels 110. The head assembly 104 may itself serve as this movable component. That is, the entire head assembly 104 may be actuated into vertical movement toward and away from the vessel support member 106 by manual, automated or semi-automated means. Alternatively or additionally, other movable components 138 such as a driven platform may be provided to support one or more of the operative components 114, 118, 120, 122 and lower and raise the components 114, 118, 120, 122 relative to the vessels 110 at desired times. One type of movable component may be provided to move one type of operative component (e.g., stirring elements 114) while another type of movable component may be provided to move another type of operative component (e.g., media dispensing cannulas 118 and/or media aspirating cannulas 120). Moreover, a given movable component may include means for separately actuating the movement of a given type of operative component 114, 118, 120, 122. For example, each media dispensing cannula 118 or media aspirating cannula 120 may be movable into and out from its corresponding vessel 110 independently from the other cannulas 118 or 120.

The media dispensing cannulas 118 and the media aspirating cannulas 120 communicate with a pump assembly (not shown) via fluid lines (e.g., conduits, tubing, etc.). The pump assembly may be provided in the head assembly 104 or as a separate module supported elsewhere by the frame 102 of the dissolution test apparatus 100, or as a separate module located external to the frame 102. The pump assembly may include separate pumps for each media dispensing line and/or for each media aspirating line. The pumps may be of any suitable design, one example being the peristaltic type. The media dispensing cannulas 118 and the media aspirating cannulas 120 may constitute the distal end sections of corresponding fluid lines and may have any suitable configuration for dispensing or aspirating liquid (e.g., tubes, hollow probes, nozzles, etc.). In the present context, the term "cannula" simply designates a small liquid conduit of any form that is insertable into a vessel 110.

In a typical operation, each vessel 110 is filled with a predetermined volume of dissolution media by pumping media to the media dispensing cannulas 118 from a suitable media reservoir or other source (not shown). One of the vessels 110 may be utilized as a blank vessel and another as a standard vessel in accordance with known dissolution testing procedures. Dosage units are dropped either manually or automatically into one or more selected media-containing vessels 110, and each stifling element 114 (or other agitation or USP-type device) is rotated within its vessel 110 at a predetermined rate and duration within the test solution as the dosage units dissolve. In other types of tests, a cylindrical basket or cylinder (not shown) loaded with a dosage unit is substituted for each stifling element 114 and rotates or reciprocates within the test solution. For any given vessel 110, the temperature of the media may be maintained at a prescribed temperature (e.g., approximately 37+/−0.5° C.) if certain USP dissolution methods are being conducted. The mixing speed of the stifling element 114 may also be maintained for similar purposes. Media temperature is maintained by immersion of each vessel 110 in the water bath of water bath container 108, or alternatively by direct heating as described previously. The various operative components 114, 118, 120, 122 provided may operate continuously in the vessels 110 during test runs. Alternatively, the operative components 114, 118, 120, 122 may be lowered manually or by an automated assembly 104 or 138 into the corresponding vessels 110, left to remain in the vessels 110 only while sample measurements are being taken at allotted times, and at all other times kept outside of the media contained in the vessels 110. In some implementations, submerging the operative components 114, 118, 120, 122 in the vessel media at intervals may reduce adverse effects attributed to the presence of the operative components 114, 118, 120, 122 within the vessels 110. During a dissolution test, sample aliquots of media may be pumped from the vessels 110 via the media aspiration cannulas 120 and conducted to an analyzing device (not shown) such as, for example, a spectrophotometer to measure analyte concentration from which dissolution rate data may be generated. In some procedures, the samples taken from the vessels 110 are then returned to the vessels 110 via the media dispensing cannulas 118 or separate media return conduits. Alternatively, sample concentration may be measured directly in the vessels 110 by providing fiber-optic probes as appreciated by persons skilled in the art. After a dissolution test is completed, the media contained in the vessels 110 may be removed via the media aspiration cannulas 120 or separate media removal conduits.

Figure 2:
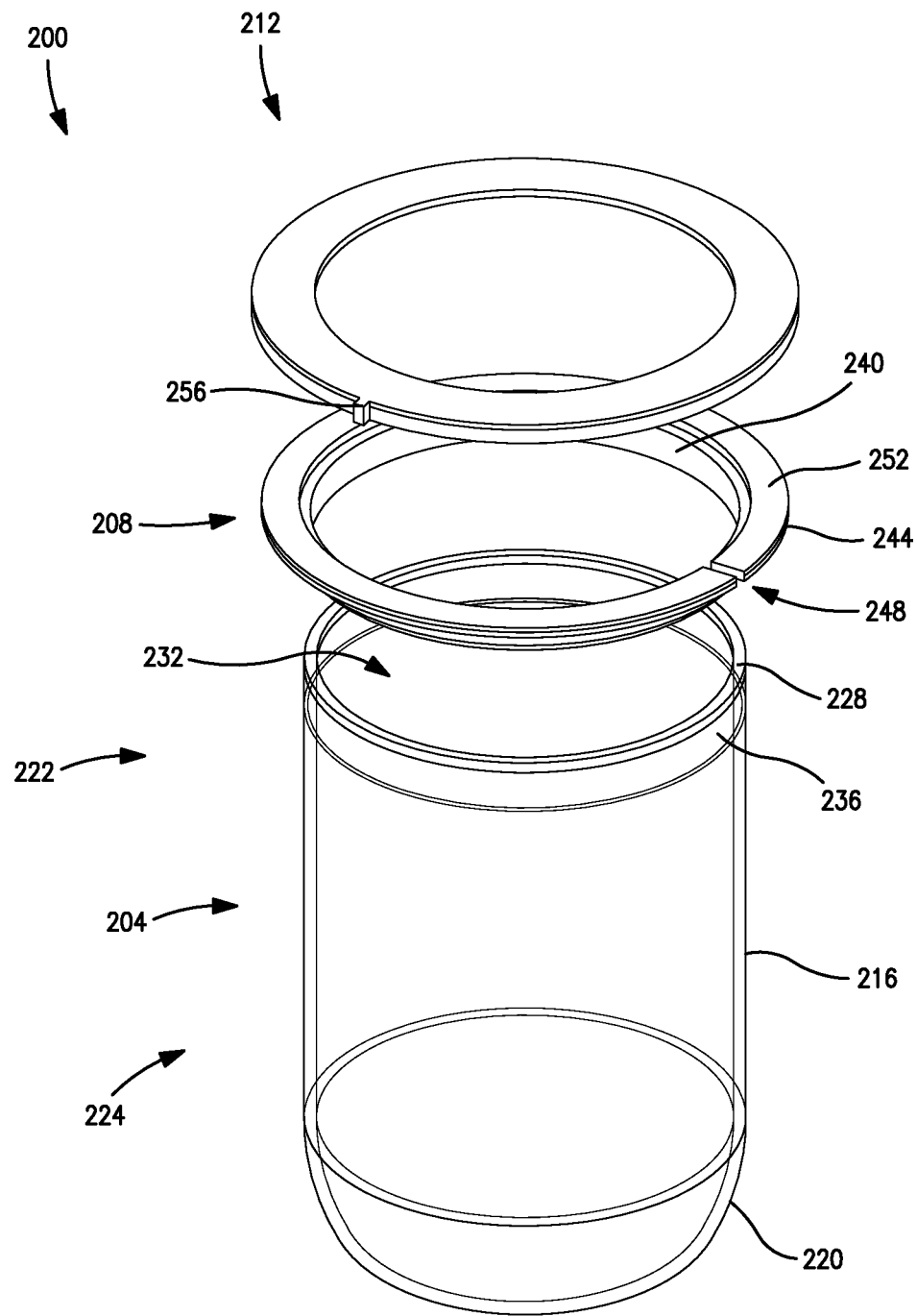
FIG. 2 is an exploded view of a vessel in unassembled form according an implementation taught in the present disclosure.

FIG. 2 is an exploded view of a vessel 200 with self-centering features according to the present teachings. The vessel 200 may be operatively installed in a dissolution test apparatus such as described above and illustrated in FIG. 1. The vessel 200 generally includes a vessel body 204, a lower ring 208 and an upper ring 212. The vessel body 204 includes a cylindrical section 216 and an adjoining bottom section 220. The cylindrical section 216 generally includes an upper end region 222 and a lower end region 224 axially spaced from the upper end region 222. The upper end region 222 terminates at a vessel rim 228 that circumscribes an upper opening 232 of the vessel 200. A groove 236 is formed around the circumference of the cylindrical section 216. The groove 236 may be located proximate or adjacent to the vessel rim 228. The bottom section 220 adjoins the cylindrical section 216 at the lower end region 224. The bottom section 220 may be generally hemispherical as illustrated or may have an alternate shape. For example, the bottom section 220 may be flat, dimpled, or have a peak extending upwardly into the interior of the vessel 200.

The lower ring 208 may include an annular lateral portion 240 and an annular flange portion 244. The diameter of the lower ring 208 is such that the lateral portion 240 fits into the vessel groove 236 around the outside of the vessel 200. When installed in the vessel groove 236, the lateral portion 240 is concentric with the inside vessel surface. The annular flange portion 244 extends in a radial direction outward from the lateral portion 240 and is generally perpendicular to the lateral portion 240. The lower ring 208 may have a gap 248 defined between respective lateral end surfaces of the lower ring 208. The gap 248 allows the lower ring 208 to be flexible so as to facilitate installation of the lower ring 208 into the vessel groove 236. The gap 248 can be increased by manipulating the lower ring 208, thereby enabling the lower ring 208 to be moved around (or past) the vessel rim 228 and into the vessel groove 236. The upper ring 212 is sized to fit onto an upper surface 252 of the lower ring 208 and is configured to secure the lower ring 208 to the vessel 200. For this purpose, the upper ring 212 may be securely engaged to the lower ring 208 by any suitable means. In one implementation, the upper ring 212 is glued to the upper surface 252 of the lower ring 208. In other implementations, secure engagement may be accomplished by other means such as, for example, screws, rivets, heat staking, ultrasonic welding, solvent welding, etc. The upper ring 212 may include means for indicating the position of the vessel 200 when the vessel 200 is mounted to a vessel plate. In the illustrated example, a tab or protrusion 256 extending in a radial direction outward from the upper ring 212 provides such means.

In a typical implementation, the vessel body 204 is fabricated from a glass material having a composition suitable for dissolution testing or other analytical techniques as appreciated by persons skilled in the art. In one implementation, a lathe or other suitable tool may be mounted to the vessel body 204 such that the cutting element of the lathe can be moved in desired directions relative to the vessel body. The lathe is employed to grind or cut the glass down to form the vessel groove 236 such that the vessel groove 236 is parallel with the inside vessel surface. In a typical implementation, the lower ring 208 and the upper ring 212 are composed of a polymeric material and fabricated by any suitable process (e.g., molding, extrusion, etc.).

Figure 3:
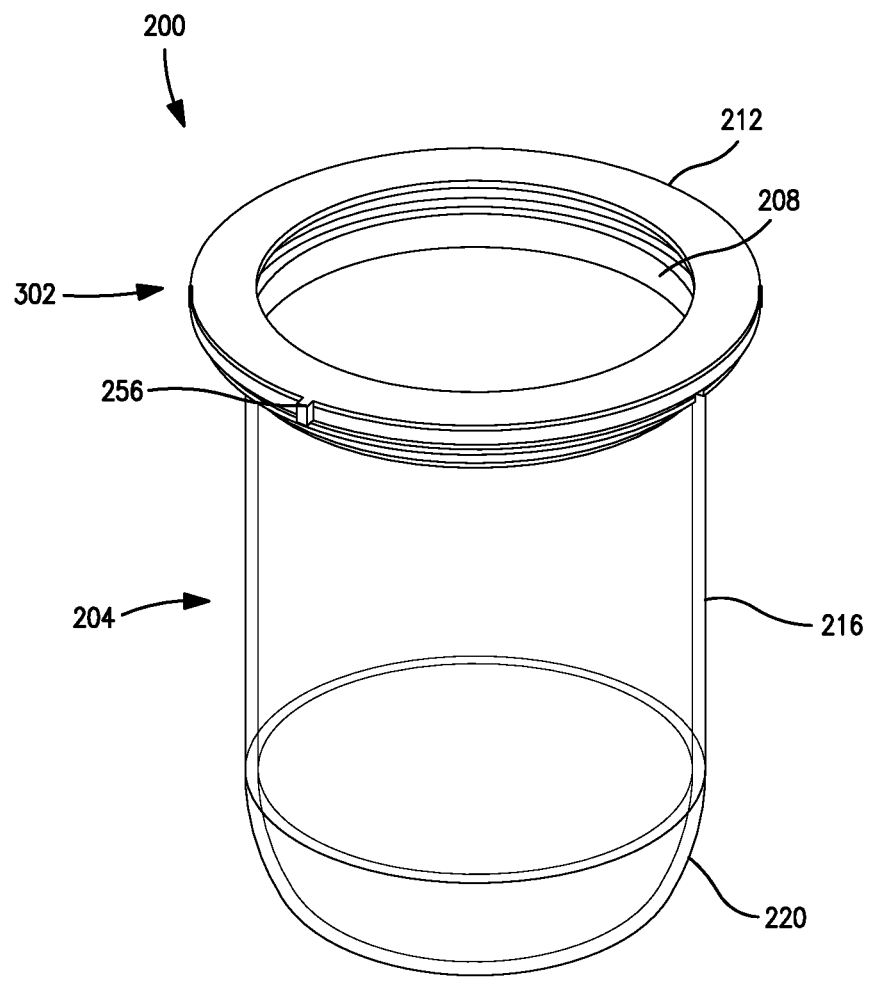
FIG. 3 is a perspective view of an example of the vessel illustrated in FIG. 2 in assembled form.
Figure 4:
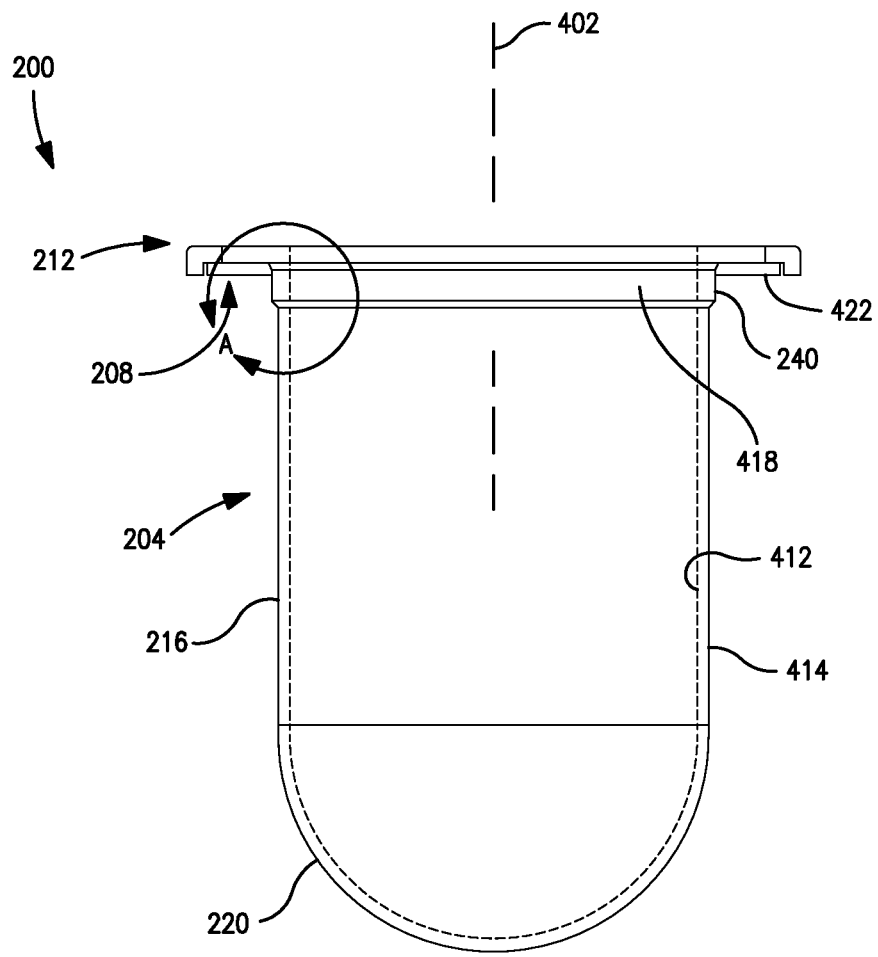
FIG. 4 is an elevation view of the vessel illustrated in FIG. 3.

FIGS. 3 and 4 are respective perspective and elevation views of the vessel 200 after the lower ring 208 and the upper ring 212 have been assembled with the vessel body 204. As shown in FIG. 3, the lower ring 208 and the upper ring 212 when assembled together cooperatively form a flange 302 of the vessel 200. As shown in FIG. 4, the vessel 200 is symmetrical about a central axis 402. The cylindrical section 210, the lower ring 208 and the upper ring 212 are thus coaxially disposed about the central axis 402. The cylindrical section 210 includes an inside vessel surface 412 facing the interior of the vessel 200 and an opposing outside vessel surface 414. The vessel body 204 is fabricated such that the inside vessel surface 412 is parallel with the central axis 402 to a high degree of precision. The lateral portion 240 of the lower ring 208 includes an outside lateral surface 418 opposite to the inside surface of the lateral portion 240 in contact with the vessel groove 236 (FIG. 2). The flange portion 244 of the lower ring 208 includes a lower flange surface 422 facing in the downward direction. The lower ring 208 is fabricated such that the outside lateral surface 418 is parallel, with the inside vessel surface 412 and the lower flange surface 422 is flat and perpendicular to the inside vessel surface 412 and the outside lateral surface 418. The accuracy of the flatness and perpendicularity of the lower flange surface 422 ensures that the vessel 200, including its central axis 402 and inside vessel surface 412, is precisely vertical when the lower ring 208 rests on a horizontal surface of a vessel supporting structure such as may be provided as part of a dissolution test apparatus or other instrument. In other words, the lower flange surface 422 is flat to a very high degree of accuracy or precision, such that the entirety of the lower flange surface 422 lies in a horizontal plane. In one example, considering a horizontal plane that is exactly perpendicular to the central axis 402 or the inside vessel surface 412, the lower flange surface 422 is coplanar with the horizontal plane to within an accuracy of $\pm 0.020°$. This generally means that the maximum amount by which any part of the lower flange surface 422 deviates (e.g., projects above or below, or tilts) from the horizontal plane is $0.020°$.

Figure 5:
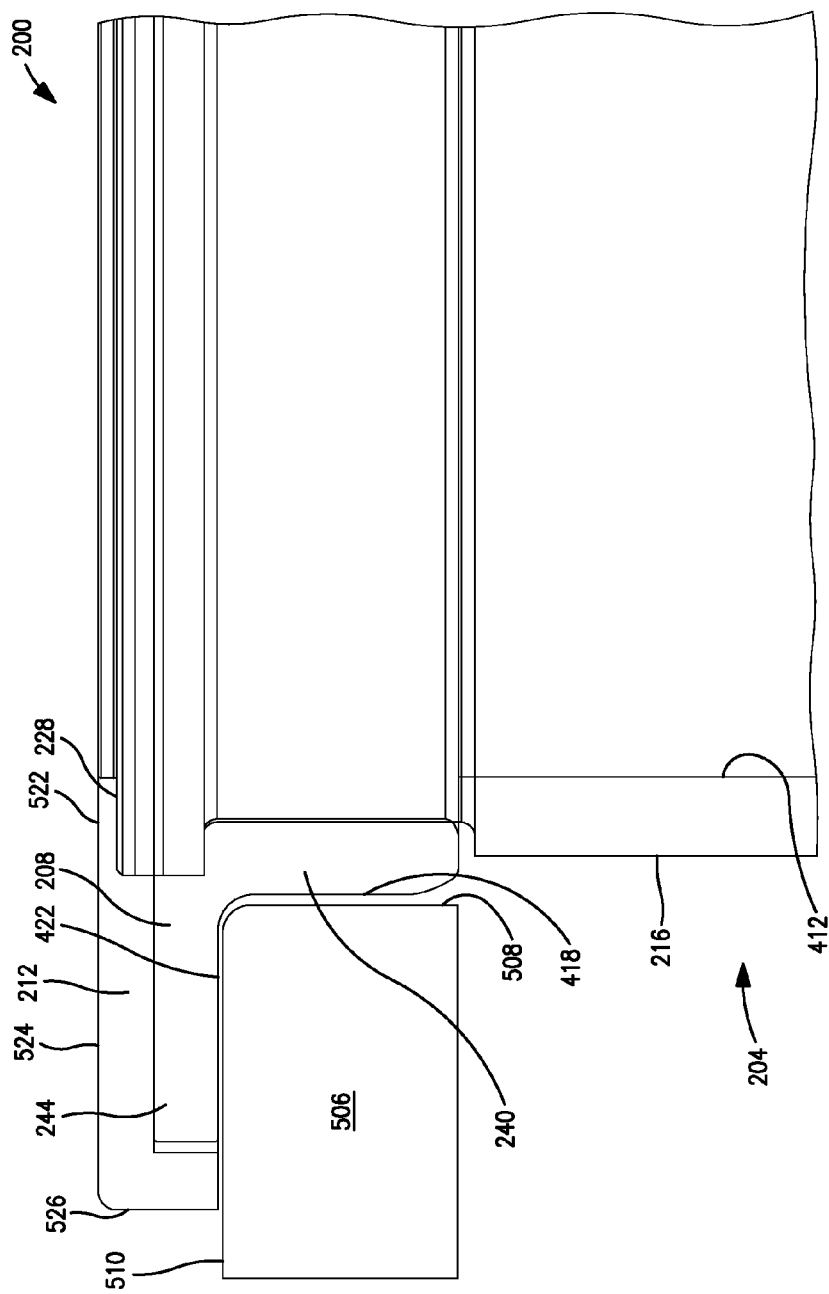
FIG. 5 is a detailed elevation view of the region of the vessel designated "A" in FIG. 4.

FIG. 5 is a detailed elevation view of the region of the vessel 200 designated A in FIG. 4 that includes the upper ring 212 and the lower ring 208. FIG. 5 also illustrates the interface between the vessel 200 and a vessel support member 506 (or vessel mounting member, or vessel locating member) at which the vessel 200 is mounted. As noted earlier, the vessel support member 506 includes one or more vessel mounting sites at which a like number of vessels may be mounted. At each vessel mounting site, an inside edge or wall 508 of the vessel support member 506 defines an aperture through which the vessel 200 extends. The flange portion 244 of the lower ring 208 extends over a top surface 510 of the vessel support member 506 at the periphery of the aperture. The lower flange surface 422 of the lower ring 208 rests directly on the top surface 510 whereby the vessel support member 506 supports the weight of the vessel 200 and any liquid contained therein. In the installed position of the vessel 200, the outside lateral surface 418 of the lower ring 208 is in contact with the inside edge 508 of the aperture. The outside lateral surface 418 is parallel to the inside vessel surface 412, the central (vertical) axis of the vessel and the inside edge 508 of the aperture, thereby ensuring the verticality and concentricity of the installed vessel 200. As another advantage of providing an initially "flange-less" vessel 200 to which the upper ring 212 and the lower ring 208 is assembled, the vessel support member 506 does not contact the glass portion of the vessel 200. Consequently, the risk of chipping, cracking or breaking the glass portion of the vessel 200 during installation or removal of the vessel 200 is greatly reduced.

In the illustrated example, an inner section 522 of the upper ring 212 extends over all or at least a portion of the vessel rim 228, and an outer section 524 of the upper ring 212 extends over all or as least a portion of the lower ring 208. Hence, when the upper ring 212 is securely engaged to the lower ring 208 such as by gluing or other fastening or engaging means, the upper ring 212 and the lower ring 208 are securely assembled together and to the vessel body 204 to form the completed vessel 200, with the vessel rim 228 enclosed by the inner section 522 of the upper ring 212 and the lateral portion 240 of the lower ring 208. Optionally, the inner section 522 may also be glued to the vessel rim 228. Also in the illustrated example, the upper ring 212 further includes an annular section 526 at or near its outside diameter that extends downward to enclose the lower ring 208.

Figure 6:
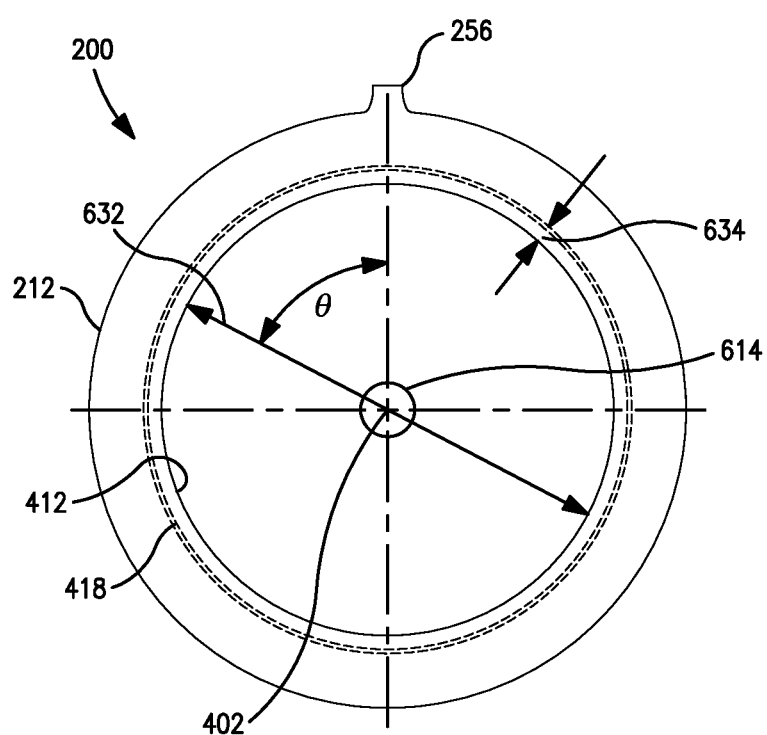
FIG. 6 is a top plan view of the vessel illustrated in FIGS. 3 and 4.

FIG. 6 is a top plan view of the vessel 200 and demonstrates the concentricity of the outside lateral surface 418 and the inside vessel surface 412. This concentricity is uniform at all circumferential points (or angular positions) relative to the central axis 402. That is, as one moves along a reference circumference (for example, the outside lateral surface 418 or the inside vessel surface 412) at polar angles $\theta$ from $0°$ to $360°$, the concentricity is maintained. The uniformity or preciseness of the concentricity ensures that when the vessel 200 is mounted at a vessel plate with a properly dimensioned aperture, the vessel 200 is completely centered at any polar angle. In other words, both the inside vessel surface 412 and the outside lateral surface 418 are concentric relative to the central axis 402 at any circumferential position at which the vessel 200 may have been installed in the aperture of the vessel plate. The vessel 200 will likewise be centered relative to the aperture of the vessel plate. Stated differently, the central axis 402 of the vessel 200 will be coaxial or collinear with the central axis of the aperture. Moreover, if an elongated structure 614 such as the shaft of an instrument to be operated within the vessel 200 (for example, a paddle- or basket-type instrument) is inserted into the vessel 200 along the central axis 402, the concentricity of both the inside vessel surface 412 and the outside lateral surface 418 relative to the elongated structure 614 will also be uniform.

One way of expressing the uniformity or preciseness of the above-described concentricity is to consider the diametric difference between the inside diameter of the vessel 200 and the outside diameter of the lateral portion 240 of the lower ring 208. In FIG. 6, the inside diameter of the vessel 200 as defined by the inside vessel surface 412 is indicated at 632. The outside lateral surface 418 defines the outside diameter of the lateral portion 240 of the lower ring 208. The diametric difference is indicated at 634. In one example, the diametric difference 634 varies or deviates (i.e., the tolerance) by an amount +/−0.05 inch (50 mils) around any referential circumference (i.e., as one moves along polar angles θ from 0° to 360°). In another example, the diametric difference 634 varies by +/−0.01 inch (10 mils). In another example, the diametric difference 634 varies by +/−0.005 inch (5 mils).

FIG. 6 also illustrates the usefulness of providing a tab 256 or other vessel locating or indexing means. As an example, the vessel 200 may be installed in a vessel plate such that the tab 256 is located at the zero-degree angular position, which may be visualized by the user relative to some reference point on the vessel plate or other nearby component of the dissolution test apparatus. If the vessel 200 then needs to be removed for cleaning or other purpose, the vessel 200 may thereafter be reinstalled in the vessel plate at the exact same angular position as before (e.g., the zero-degree position). This feature may further enhance the preciseness of the installation and promote accurate data acquisition and repeatability of experiments.

The self-centering vessel 200 disclosed herein may be installed in any type of vessel plate and does not require the apertures of typical, commercially available vessel plate to be modified. The vessel 200 is compatible with known types of vessel retaining devices. As appreciated by persons skilled in the art, a vessel retaining device may be utilized for retaining the vessel 200 in its operative mounted position in the aperture of the vessel support member to prevent the vessel 200 from moving vertically out from the aperture after the vessel 200 has been properly installed. A vessel retaining device is therefore particularly useful in conjunction with the use of a liquid bath as described above and illustrated in FIG. 1, as the vessel retaining device prevents the vessel 200 from "popping out" of the aperture due to buoyancy effects. As one known example, a vessel retaining device may include a ring-shaped member. After lowering a vessel 200 through the aperture of the vessel support member, the ring-shaped member is lowered onto the flange 302 of the vessel 200. The ring-shaped member is configured to interact with posts or pins affixed to the vessel support member in a manner that locks the vessel 200 in place vertically at the vessel mounting site.

The vessel 200 may be assembled in the manner described above in conjunction with FIGS. 2-5. The vessel body 204 is formed typically from a glass material, and the lower ring 208 and upper ring 212 are formed typically from polymeric materials. The lower ring 208 is then fitted in the vessel groove 236 and the upper ring 212 is secured to the lower ring 208 whereby the resulting flange 302 is securely engaged with the vessel body 204 and the vessel 200 is thereby fully assembled, all as described above. One or more vessels 200 may then be installed at respective vessel mounting sites of a dissolution test apparatus such as illustrated in FIG. 1, and the vessels 200 may then be utilized to acquire dissolution data by operating the dissolution test apparatus as described above.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A vessel comprising:
a cylindrical section coaxially disposed about a central axis of the vessel, the cylindrical section comprising an inside vessel surface, an outside vessel surface, an upper end region terminating at a rim circumscribing a vessel opening, a vessel groove formed at the outside vessel surface in the upper end region, and a lower end region axially spaced from the upper end region;
a bottom section disposed at the lower end region; and
a flange configured for supporting the vessel at a vessel mounting site, the flange comprising:
a lower ring comprising an annular lateral portion and an annular flange portion, the lateral portion disposed in the vessel groove and comprising an outside lateral surface concentric with the inside vessel surface, the flange portion comprising an upper flange surface and a lower flange surface perpendicular to the inside vessel surface, wherein the flange portion has an outer flange diameter greater than the outer vessel diameter, and the lower ring terminates at a pair of opposing lateral end surfaces separated by a gap; and
an upper ring comprising an inner section extending over at least a portion of the rim, and an outer section securely engaged with the upper flange surface.

2. The vessel of claim 1, wherein the upper ring comprises means for marking an angular position of the vessel relative to the central axis.

3. The vessel of claim 1, wherein the upper ring comprises a protrusion extending in a radial direction from flange portion.

4. The vessel of claim 1, wherein the central axis is a vertical axis passing through a horizontal plane, and the lower flange surface is entirely coplanar with the horizontal plane to within an accuracy of ±0.020°.

5. The vessel of claim 1, wherein the inside vessel surface defines an inside vessel diameter of the cylindrical section, the outside lateral surface defines an outside lateral diameter of the lateral portion, and the diametric difference between the inside vessel diameter and the outside lateral diameter is uniform at any circumferential point relative to the central axis.

6. The vessel of claim 1, wherein the inside vessel surface defines an inside vessel diameter of the cylindrical section, the outer lateral surface defines an outside lateral diameter of the lateral portion, and the diametric difference between the inside vessel diameter and the outside lateral diameter varies by no greater than +/−0.05 inch at any circumferential point relative to the central axis.

7. A dissolution test apparatus comprising:
a vessel support member comprising a top surface and an inside edge circumscribing an aperture; and
a vessel extending through the aperture and comprising:

a cylindrical section coaxially disposed about a central axis of the vessel, the cylindrical section comprising an inside vessel surface, an outside vessel surface, an upper end region terminating at a rim circumscribing a vessel opening, a vessel groove formed at the outside surface in the upper end region, and a lower end region axially spaced from the upper end region;

a bottom section disposed at the lower end region; and a lower ring comprising an annular lateral portion and an annular flange portion, the lateral portion disposed in the vessel groove and comprising an outer lateral surface concentric with the inside vessel surface and contacting the inside edge of the aperture, the flange portion comprising an upper flange surface and a lower flange surface perpendicular to the inside vessel surface; and an upper ring comprising an inner section extending over at least a portion of the rim, and an outer section securely engaged with the upper flange surface, wherein the inside vessel surface is parallel to the inside edge of the vessel support member.

8. The dissolution test apparatus of claim 7, wherein the lower ring terminates at a pair of opposing lateral end surfaces separated by a gap.

9. The dissolution test apparatus of claim 7, wherein the upper ring comprises means for marking an angular position of the vessel relative to the central axis.

10. The dissolution test apparatus of claim 7, wherein the inside vessel surface defines an inside vessel diameter of the cylindrical section, the outside lateral surface defines an outside lateral diameter of the lateral portion, and the diametric difference between the inside vessel diameter and the outside lateral diameter is uniform at any circumferential point relative to the central axis.

11. The dissolution test apparatus of claim 7, further comprising an elongated structure extending into the vessel, wherein the outer lateral surface and the inside vessel surface are concentric with the elongated structure.

12. The dissolution test apparatus of claim 7, further comprising an elongated structure extending into the vessel, wherein the inside vessel surface is parallel with the elongated structure.

13. A method for assembling a vessel, the vessel comprising a cylindrical section coaxially disposed about a central axis of the vessel and including an upper end region terminating at a rim circumscribing a vessel opening and a lower end region, and a bottom section disposed at the lower end region, the method comprising:

mounting a lower ring to the vessel such that an annular lateral portion of the lower ring is disposed in a vessel groove formed at an outside vessel surface of the vessel, wherein an outside lateral surface of the lateral portion is concentric with an inside vessel surface of the vessel, the lower ring further comprising a flange portion including a lower flange surface perpendicular to the inside vessel surface, the flange portion having an outer flange diameter greater than an outer vessel diameter of the cylindrical section; and mounting an upper ring to the vessel such that an inner section of the upper ring extends over at least a portion of the rim, and an outer section of the upper ring is securely engaged with an upper flange surface of the flange portion, wherein the lower ring and the upper ring form a flange configured for supporting the vessel at a vessel mounting site, and wherein the lower ring terminates at a pair of opposing lateral end surfaces separated by a gap, and mounting the lower ring further comprises increasing the gap to facilitate moving the lower ring past the rim and into the vessel groove.

* * * * *